United States Patent [19]

Kirch et al.

[11] 4,280,928

[45] Jul. 28, 1981

[54] CATALYST COMPOSITIONS AND THEIR USE FOR THE PREPARATION OF METHACROLEIN

[75] Inventors: Lawrence S. Kirch, Huntingdon Valley; William J. Kennelly, Newtown, both of Pa.

[73] Assignee: Rohm and Haas Company, Philadelphia, Pa.

[21] Appl. No.: 84,254

[22] Filed: Oct. 12, 1979

[51] Int. Cl.$^3$ .................... B01J 21/02; B01J 23/28; B01J 27/14; B01J 23/02

[52] U.S. Cl. .................... 252/432; 252/435; 252/437; 252/439

[58] Field of Search ............ 252/432, 435, 437, 431 P, 252/439

[56] References Cited

U.S. PATENT DOCUMENTS

| | | | |
|---|---|---|---|
| 3,171,859 | 3/1965 | Sennewald et al. | 260/604 R |
| 3,238,254 | 3/1966 | Kerr | 260/603 |
| 3,313,856 | 4/1967 | Phielix et al. | 260/604 R |
| 3,325,516 | 6/1967 | Fettis et al. | 260/604 R |
| 3,429,930 | 2/1969 | Heslan | 260/604 R |
| 3,454,630 | 7/1969 | Yamaguchi et al. | 260/604 R |
| 3,471,556 | 10/1969 | Yamaguchi et al. | 260/603 R |
| 3,485,878 | 12/1969 | Heslan | 260/604 R |
| 3,576,764 | 4/1971 | Yamaguchi et al. | 260/604 R |
| 3,764,632 | 10/1973 | Takenaka et al. | 260/604 R |
| 3,925,464 | 12/1975 | Oda et al. | 260/530 N |
| 3,932,551 | 1/1976 | Grasselli et al. | 260/680 E |
| 3,956,377 | 5/1976 | Dohhyj et al. | 260/530 N |
| 3,959,384 | 5/1976 | Takenaka et al. | 260/604 R |
| 3,966,802 | 6/1976 | Takenaka et al. | 260/604 R |
| 3,966,823 | 6/1976 | Takenaka et al. | 260/604 R |
| 3,972,920 | 8/1976 | Ishii et al. | 260/603 C |
| 3,976,688 | 8/1976 | Zeon et al. | 260/530 N |
| 3,997,600 | 12/1976 | Feriazzo et al. | 260/530 N |
| 4,014,925 | 3/1977 | Feriazzo et al. | 260/486 R |
| 4,025,549 | 5/1977 | Feriazzo et al. | 260/486 R |
| 4,035,418 | 7/1977 | Okada et al. | 260/603 C |
| 4,039,583 | 8/1977 | Kawakami et al. | 260/604 R |
| 4,049,575 | 9/1977 | Sasaki et al. | 252/439 |
| 4,051,179 | 9/1977 | Sonobe et al. | 260/530 N |
| 4,051,180 | 9/1977 | Shaw et al. | 260/530 N |
| 4,052,332 | 10/1977 | D'Amore et al. | 252/413 |
| 4,065,507 | 12/1977 | Hardman et al. | 260/603 C |
| 4,066,704 | 1/1978 | Harris et al. | 260/604 R |
| 4,070,397 | 1/1978 | White et al. | 260/530 N |
| 4,075,244 | 2/1978 | Akiyama et al. | 260/530 N |
| 4,082,698 | 4/1978 | Shaw et al. | 252/469 |
| 4,083,804 | 4/1978 | Saito et al. | 252/432 |
| 4,110,369 | 8/1978 | White | 260/530 N |
| 4,111,983 | 8/1978 | Kurtz et al. | 562/535 |
| 4,111,984 | 8/1978 | Ishii et al. | 562/538 |
| 4,111,985 | 8/1978 | Okada et al. | 562/546 |
| 4,124,634 | 11/1978 | Gotoh et al. | 562/532 |
| 4,136,110 | 1/1979 | White et al. | 562/532 |
| 4,148,758 | 4/1979 | Brazdil et al. | 252/432 |
| 4,162,234 | 7/1979 | Grasselli et al. | 260/604 R |

*Primary Examiner*—Werren B. Lone
*Attorney, Agent, or Firm*—Terence P. Strobaugh; George W. F. Simmons; Robert A. Doherty

[57] ABSTRACT

Methacrolein is produced by the catalytic vapor phase oxidation of isobutylene (including compounds converted to isobutylene). The catalyst has the following formula: $Mo_aP_bFe_cCo_dNi_eBi_fTe_gSb_hCs_iZr_jX_kO_x$ wherein a-k represent the number of atoms of the particular element depicted, X is another element and x is the number of oxygens present.

9 Claims, No Drawings

CATALYST COMPOSITIONS AND THEIR USE FOR THE PREPARATION OF METHACROLEIN

This invention relates to novel catalyst compositions for the preparation of methacrolein by the vapor phase oxidation of isobutylene including compounds which can be converted to isobutylene such as tert-butyl alcohol, tert-butyl acetate, methyl tert-butyl ether and the like.

Many catalysts and many procedures are known for preparing methacrolein and other unsaturated aldehydes. The following is a list of U.S. patents which disclose one or the other U.S. Pat. Nos. 3,966,823; 3,972,920; 4,035,418; 4,049,575; 4,065,507; 4,083,804; 4,111,984, 4,111,985, and 4,148,757. However, none of these patents disclose the specific catalyst composition of this invention.

SUMMARY OF THE INVENTION

It is the object of this invention to produce methacrolein by the vapor phase oxidation of isobutylene, including compounds which are converted to isobutylene, in the presence of molecular oxygen, optionally, in the presence of steam by passing the reaction mixture over a catalyst at a temperature in the range of from about 200° to about 600° C. wherein said catalyst has a composition represented by the formula:

$$Mo_aP_bFe_cCo_dNi_eBi_fTe_gSb_hCs_iZr_jX_kO_x$$

wherein X is one or more elements selected from Cu, B, Al, K, La, Pr, Ru, V, W or Y and when a is 12; b is a number from 1.5 to 2.5; c is a number from 0 to 7; d is a number from 1 to 7; e is a number from 1 to 6; f is a number from 0.5 to 1.5; g is a number from 0.5 to 2; h is a number from 0 to 1; i is a number from 0 to 1; j is a number from 0 to 2; k is a number from 0 to 2.0. and x is the number of oxygens required to satisfy the valence requirements of the other elements present.

Preferred catalyst compositions of this invention are those of the formula $Mo_aP_bFe_cCo_dNi_eBi_fTe_gSb_hCs_iZr_jX_kO_x$ wherein when a is 12; b is 2; c is 1–7; d is 3–7; e is 1–5; f is 1; g is 0.7–1.4; h is 0–1; i is 0.5; j is 0–1.75; k is 0–1; x is the number of oxygens required to satisfy the valence requirements of the other elements present and X is one or more elements selected from Cu, B or Al.

The most preferred catalyst compositions are those represented by the formula:

$$Mo_{12}P_2Fe_{5-7}Co_{5-7}NiBiSbZr_{1-1.75}Cs_{0.5}Te_{0.7}O_x.$$

The catalyst and the invention may be employed in the supported or unsupported form. If a support is employed, any known support such as alumina, pumice, silicon carbide, zirconia, silica, alumina-silica, perlite and the like that are stable under the reaction conditions may be employed. Silica is the preferred carrier.

The catalysts of the invention may be made by several techniques including coprecipitation of soluble salts. The metal oxides can be blended together, or can be formed separately and then blended, or formed separately or together in situ. Promoter oxides are preferably incorporated into the catalyst by blending into the gel before calcining or by blending into the oven-dried base catalyst before calcining. A preferred manner of incorporating promoter elements is by choosing a water-soluble salt of the promoter element, forming an aqueous solution of the salt, and mixing the solution with a solution or a suspension of the base elements or salts thereof. Optionally, the promoter elements may be incorporated by the use of soluble complex salts or compounds with the desired base elements which upon calcination will yield the desired ratio of the elements in the finished catalyst. If necessary, some of the aqueous solutions are heated to facilitate solution. After agitating for a short time, aqueous ammonium hydroxide is added. The slurry is stripped, dried and crushed and calcined at a temperature in the range of from about 400° to about 750° C. and, preferably, in the range of from about 500° to about 650° in the presence of an air stream. The most preferred calcining temperature is in the range of from about 550° to about 600° C.

We have discovered that in the process for preparing the catalysts that by heating the solution containing molybdenum at about 70° C. for one hour after all the compounds of the one solution (including carrier) (identified as Solution A in the examples) that increased methacrolein yields are obtained.

As a source for molybdenum in the preparation of the catalyst, an oxide or a compound convertible on heating into an oxide is desirable, for example, ammonium heptamolybdate and the like. As a source for antimony, oxides, hydrated oxides, chlorides and the like are preferred. As a source for bismuth, iron, nickel and alkali metal, oxides or compounds convertible on heating into oxides such as nitrates, and the like are preferred. As the carriers, silica, alumina or silicon carbide may be used.

In the process of the present invention a mixture of the feed in vapor form and molecular oxygen, optionally in the presence of steam or other diluents, is contacted with a catalyst of the above composition, at an elevated temperature of about 200°–600° C., for a contact time sufficient to convert the feed mainly to methacrolein the reactor effluent may contain methacrylic acid. The contact time may vary widely, from 1 to 20 seconds or more. The reaction can be conducted under atmospheric, superatmospheric or subatmospheric pressures. However, in general, pressures near atmospheric, i.e., −10 to 100 psig are preferred.

Any source of oxygen may be employed in the process, and for economic reasons, it is preferred that air be employed as the source of oxygen. The molar ratio of oxygen to the starting compounds may range between 0.5:1 to 10:1 with the preferred ratio being in the range of from about 1:1 to about 5:1.

Diluents, such as water, nitrogen and carbon dioxide, may be present in the reaction mixture.

In general, any apparatus of the type suitable for carrying out oxidation reactions in the vapor phase may be employed in the execution of this process. The processes may be conducted either continuously or intermittently. The catalyst bed may be a fixed-bed employing a large particulate or pelleted catalyst, or in the alternative, a so-called "fluidized" bed of catalyst may be employed.

The reactor may be brought to the reaction temperature before or after the introduction of the reaction feed mixture. However, in a large scale operation, it is preferred to carry out the process in a continuous manner, and in such a system the recirculation of any unreacted starting material is contemplated.

The products of the reaction may be recovered by any of the methods known to those skilled in the art. One such method involves scrubbing the effluent gases from the reactor with cold water or an appropriate solvent to remove the products of the reaction. The ultimate recovery of the products may be accomplished by conventional means, such as by distillation or solvent extraction.

The term "isobutylene" includes compounds which are converted or can be converted to isobutylene such as tert-butanol, tert-butyl acetate, tert-butyl-methyl ether and the like.

The examples disclosed in the specific embodiment are repesentative of the process conditions and catalyst compositions that are suitable for the process of this invention. However, the scope of the invention is not to be limited by these examples.

EXAMPLE 1

$Mo_{12}P_2Fe_5Co_5NiBiSbZrCs_{0.5}Te_{0.7}O_x$

In a one liter resin kettle is dissolved ammonium heptamolybdate $(NH_4)_6Mo_7O_{24}.4H_2O$ (42.8 grams), cobalt nitrate, $Co(NO_3)_2.6H_2O$ (29.2 grams), nickel nitrate, $Ni(NO_3)_2.6H_2O$ (5.8 grams) and phosphoric acid, $H_3PO_4$ (85%; 4.6 grams) in deionized water (85 ml.). The solution is heated to 70° C. and antimony pentoxide, $Sb_2O_5$ (3.25 grams), tellurium dioxide (2.2 grams), and colloidal silica (35%; 40 grams) is added. This solution is then stirred for 1 hour at 70° C.

A solution of zirconium nitrate, $Zr(NO_3)_4$ (6.8 grams) in deionized water (50 ml.) is then added to a solution containing nitric acid (71%; 10 ml.) deionized water (40 ml.) bismuth nitrate, $Bi(NO_3)_3.5H_2O$ (9.7 grams) and ferric nitrate, $Fe(NO_3)_3.9H_2O$ (40.3 grams). To this solution of bismuth nitrate, ferric nitrate and zirconium nitrate is then added cesium nitrate, $CsNO_3$ (2.0 grams). This solution is then added to the solution first prepared over a 30 minute period. Ammonium hydroxide (14%; 140 grams) is then added over a 45 minute period. The solution is evaporated to dryness and the crude catalyst is dried in a vacuum oven at 160° C. for 6 hours. The dried material is then crushed to 8 to 18 mesh particles and calcined for 8 hours at 575° C. to afford 50.0 g. of catalyst having the composition $Mo_{12}P_2Fe_5Co_5NiBiSbZrCs_{0.5}Te_{0.7}O_x$.

EXAMPLE 2

$Mo_{12}P_2Fe_5Co_5NiBiSbZrTe_{0.7}Cs_{0.5}O_x$

Three solutions are made as follows:

1. Solution A is prepared by dissolving 85.6 g of $(NH_4)_6Mo_7O_{24}.4H_2O$, 58.4 g of $Co(NO_3)_2.6H_2O$, 11.6 g of $Ni(NO_3)_2.6H_2O$, and 9.2 g of 85% $H_3PO_4$ in 170 ml of deionized water.

2. Solution B is prepared by dissolving 19.4 g of $Bi(NO_3)_3.5H_2O$ and 80.6 g of $Fe(NO_3)_3.9H_2O$ in 100 ml of a solution containing 20 ml of 75% $HNO_3$ and the balance, deionized water.

3. Solution C is prepared by dissolving 13.6 g of $Zr(NO_3)_4$ in 100 ml of deionized water.

Solution A is heated to 70° C. followed by addition of 6.5 g of $Sb_2O_5$, 4.4 g of $TeO_2$, and 80.0 g of 35% silica sol. Solution C is added to solution B and 4.0 g $CsNO_3$ is dissolved in the combined solutions of B and C after which the combined solution of B and C is stirred into solution A which has been heated to 70° C. for one hour. A solution of 280 g of 14% $NH_4OH$ is added to the mixture and the catalyst is evaporated to dryness and then vacuum dried at 160° C. (pressure, 10 torr). The catalyst is then ground to 8-18 mesh and calcined at 575° C. in air. The composition of the finished catalyst is $Mo_{12}P_2Fe_5Co_5Ni_1Bi_1Sb_1Zr_1Te_{0.7}Cs_{0.5}O_x$.

EXAMPLE 3

$Mo_{12}P_2Fe_5Co_5NiBiZrSbCs_{0.5}Te_{0.7}CuO_x$

Stir the following ingredients into a 1 liter resin kettle using a small amount of deionized water to aid in transferring: 42.8 g ammonium heptamolybdate, 20 ml of 71% $HNO_3$, 9.7 g of bismuth nitrate in 8 ml of 71% $HNO_3$, and 2.0 g of cesium nitrate. Dissolve 40.3 g of ferric nitrate, 29.2 g of cobalt nitrate 5.8 g of nickel nitrate and 4.8 g of copper nitrate in 75 ml of deionized water and add to the flask. Add 40.0 g of 35% colloidal silica, 6.8 g of zirconium nitrate, 2.2 g of tellurium dioxide, 3.25 g of antimony pentoxide and 4.6 g of 85% phosphoric acid. Add sufficient deionized water to bring the total water content to 190 ml. Heat the mixture to 60° C. and then add 156.5 g of 14% $NH_4OH$ over a 45 minute period. Evaporate to dryness, then vacuum dry at 160° C. for 6 hrs. Crush to 8 to 18 mesh particles and calcine at 500° C. for 8 hrs. in air. The resulting catalyst has the composition $Mo_{12}P_2Fe_5Co_5NiBiZrSbCs_{0.5}Te_{0.7}CuO_x$.

EXAMPLE 4

$Mo_{12}P_2Fe_5Co_5NiBiSbZrCs_{0.5}Te_{0.7}O_x$

Make 3 solutions as follows:

Solution A—In a 1 liter resin kettle dissolve 42.8 g of ammonium heptamolybdate, 29.2 g of cobalt nitrate, 5.8 g of nickel nitrate, and 4.6 g of 85% phosphoric acid in 85 ml of deionized water. Heat to 70° and add 3.25 g of antimony pentoxide, 2.2 g of tellurium dioxide and 40.0 g of "Nalco", 35% colloidal silica.

Solution B—In a beaker dilute 10 ml of 71% $HNO_3$ to 50 ml with deionized water. Dissolve 9.7 g of bismuth nitrate in this solution followed by 40.3 g of ferric nitrate.

Solution C—Dissolve 6.8 g of zirconium nitrate in 50 ml of deionized water.

Slowly add solution C to solution B, then dissolve 2.0 g of cesium nitrate in this combined solution. Add this solution to solution A over a 30 minute period, then add 140.0 g of 14% $NH_4OH$ over a 30 minute period. Dry and calcine as in Example 2.

EXAMPLES 5–9

The catalysts of Examples 5–9 are prepared by the procedure of Example 4 with the compositions and product distributions given below as shown in Table 1.

TABLE 1

| Ex. | Composition | Calcining Temp. °C. | Methacrolein Yield |
|---|---|---|---|
| 5 | $Mo_{12}P_2Fe_5Co_5NiBiSbZr_{0.75}Te_{0.7}Cs_{0.5}O_x$ | 500 | 37.5% |
| 6 | $Mo_{12}P_2Fe_5Co_5NiCuBiSbZrTe_{0.7}Cs_{0.5}O_x$ | 500 | 56.1% |
| 7 | $Mo_{12}P_5Fe_7Co_7NiBiSbZrTe_{0.7}Cs_{0.5}O_x$ | 500 | 69.7% |
| 8 | $Mo_{12}P_2Fe_3Co_4Ni_5CuBiSbZrTe_{0.7}Cs_{0.5}O_x$ | 500 | 67.9% |
| 9 | $Mo_{12}P_2FeCo_5Ni_5CuBiSbZrTe_{0.7}Cs_{0.5}O_x$ | 500 | 71.5% |

EXAMPLE 10

$Mo_{12}P_2Fe_7Co_7NiBiSbZr_{1.25}Cs_{0.5}Te_{0.7}$

In a one liter resin kettle is added ammonium heptamolybdate (42.8 grams) cobalt nitrate (40.9 grams), nickel nitrate (5.8 grams), phosphoric acid (4.6001 grams of 85% in 15 milliliters of deionized water) and deionized water (85 milliliters). The solution is heated to 70° C. and antimony pentoxide (3.2511 grams), tellurium dioxide (2.2 grams) and colloidal silica (35%; 40 grams) is added. This is solution A.

In a separate beaker is dissolved bismuth nitrate (9.7 grams) in a nitric acid solution (10 milliliters of 71% nitric acid and 40 milliliters of deionized water). When the bismuth nitrate has dissolved ferric nitrate (56.4 grams) is then added. This is solution B.

In another beaker is dissolved zirconium nitrate (8.5 grams) in deionized water (50 milliliters). This is solution C.

Solution C is added slowly to solution B followed by the addition of cesium nitrate (2.002 grams). This solution is then added to solution A over a 30 minute period. Ammonium hydroxide (14%; 140 grams) is then added over a 30 minute period. This solution is evaporated to dryness overnight at 70° C. The residue is vacuum dried for 6 hours at 160° C. at 10 millimeters of Hg to afford 171.4 grams of material. The dry material is crushed and screened to 8 M to 18 M. A sample weighing 47.4 grams is calcined for 8 hours at 500° C. to afford 24.2 grams of $Mo_{12}P_2Fe_7Co_7NiBiSbZr_{1.25}Cs_{0.5}Te_{0.7}O_x$.

EXAMPLE 11

$Mo_{12}P_2Fe_7Co_7NiBiSbZr_{1.5}Cs_{0.5}Te_{0.7}O_x$

By following substantially the procedure of Example 10 and the substituting for the 8.5 grams of zirconium nitrite in Example 10, 10.2 grams of zirconium nitrite, there is obtained, after calcining 52.5 grams of dry material, 27.0 grams of calcined material having the formula $Mo_{12}P_2Fe_7Co_7NiBiSbZr_{1.5}Cs_{0.5}Te_{0.7}$

EXAMPLE 12

$Mo_{12}P_2Fe_5Co_5NiBiSbZr_{1.75}Cs_{0.5}Te_{0.7}O_x$

By following substantially the procedure of Example 10 and by changing the amount of cobalt nitrate to 29.2 grams; the amount of ferric nitrate to 40.3 grams and the amount of zirconium nitrate to 11.9 grams there is obtained 24 grams of calcined material from 43.6 grams of dry material having the formula:

$Mo_{12}P_2Fe_5Co_5NiBiSbZr_{1.75}Cs_{0.5}Te_{0.7}O_x$

EXAMPLE 13

$Mo_{12}P_2Fe_7Co_7NiBiSbCs_{0.5}Te_{0.7}CuO_x$

By following substantially the procedure described in Example 3 and by eliminating the zirconium nitrate recited therein and by substituting 56.4 grams of ferric nitrate and 40.9 grams of cobalt nitrate for the quantities employed in Example 3, there is obtained 195.0 grams of dried catalyst which after grinding and screening through 8 mesh over 18 mesh screens affords 110.2 grams of material which is calcined at 500° C. for 8 hours to afford 50.3 grams of $Mo_{12}P_2Fe_7Co_7NiBiSbCs_{0.5}Te_{0.7}CuO_x$.

EXAMPLE 14

$Mo_{12}P_2Fe_5Co_5NiBiSbZr_{1.25}Cs_{0.5}Te_{0.7}O_x$

By following substantially the procedure as described in Example 4 and by substituting 8.5 grams of zirconium nitrate for the amount recited in Example 4 there is obtained 139.9 grams of dried material. Screening through 8 mesh onto 18 mesh affords 89.6 grams which is divided into two portions, one portion is calcined at 500° C. and another at 575° C. From 44.8 grams of material is obtained 25.1 grams of calcined material and from 44.4 grams of uncalcined material is obtained 25.5 grams. The catalyst has the formula $Mo_{12}P_2Fe_5Co_5NiBiSbZr_{1.25}Cs_{0.5}Te_{0.7}O_x$

EXAMPLE 15

$Mo_{12}P_2FeCo_5Ni_5BiSbZrCs_{0.5}Te_{0.7}Cu$

By following substantially the procedure of Example 3 and by substituting 8.1 grams of ferric nitrate and 29.2 grams of nickel nitrate for the amounts recited in Example 3 there is obtained a 172.5 grams of catalyst which after grinding and screening affords 110 grams on 18 mesh which after calcining for 8 hours at 500° C. affords 53.0 grams of $Mo_{12}P_2FeCo_5Ni_5BiSbZrCs_{0.5}Te_{0.7}CuO_x$

EXAMPLE 16

$Mo_{12}P_2Fe_5Co_5NiBiZrCs_{0.5}Te_{0.7}O_x$

By following substantially the procedure as described in Example 4 and by eliminating the addition of antimony pentoxide there is obtained 142.4 grams of dried material which after grinding and screening affords 87.7 grams of over 18 mesh material which after calcining for 8 hours at 575° C. affords 48.0 grams of a catalyst having the formula $Mo_{12}P_2Fe_5NiBiZrCs_{0.5}Te_{0.7}O_x$

EXAMPLE 17

$Mo_{12}P_2Fe_3Co_3Ni_5BiSbZrCs_{0.5}Te_{0.7}CuO_x$

By following substantially the procedure as described in Example 3 and by substituting 24.2 grams of ferric nitrate; 17.5 grams of cobalt nitrate and 29.2 grams of nickel nitrate for the identical materials described therein there is obtained 176.0 grams of dried catalyst which after grinding and screening through 8 mesh screen onto 18 mesh affords 119.2 grams of material which upon calcining for 8 hours at 500° C. affords 51.3 grams of $Mo_{12}P_2Fe_3Co_3Ni_5BiSbZrCs_{0.5}Te_{0.7}CuO_x$

EXAMPLE 18

$Mo_{12}P_2Fe_5Co_5NiBiSbZr_{1.5}Cs_{0.5}Te_{0.7}O_x$

By following substantially the procedure as described in Example 4 and by substituting 10.2 grams of zirconium nitrate for the amount recited therein there is obtained 153 grams of dried material which after grinding and screening through 8 mesh on 18 mesh affords 92.6 grams. This material is divided in half and 46.3 grams calcined at 500° C. to afford 25.4 grams and 46.8 grams calcined at 575° C. to afford 25.0 grams of $Mo_{12}P_2Fe_5Co_5NiBiSbZr_{1.5}Cs_{0.5}Te_{0.7}O_x$

EXAMPLE 19

$Mo_{12}P_2Fe_5Co_5NiBiSbZrCs_{0.5}Te_{0.7}Cu_{0.25}O_x$

By following substantially the procedure as described in Example 4 and by adding 1.2 grams of copper nitrate immediately following the addition of cesium nitrate there is obtained 152.0 grams of dried material which after grinding and screening through 8 mesh on 18 mesh affords 90.3 grams which after calcining for 8 hours at 500° C. affords 48.3 grams of $Mo_{12}P_2Fe_5Co_5NiBiSbZrCs_{0.5}Te_{0.7}Cu_{0.25}O_x$

EXAMPLE 20

$Mo_{12}P_2Fe_5Co_5NiBiSbZrCs_{0.5}Te_{0.7}Al_{0.5}O_x$

By following substantially the procedure as described in Example 4 and by additionally adding 3.75 grams of aluminum nitrate immediately following the addition of cesium nitrate there is obtained 143.9 grams of dried material which after crushing and screening through 8 mesh on 18 mesh affords 83.9 grams which after calcining for 8 hours at 500° C. affords 47.5 grams of $Mo_{12}P_2Fe_5Co_5NiBiSbZrCs_{0.5}Te_{0.7}Al_{0.5}O_x$ By following substantially the procedure of Example 3 and by employing the amounts of compounds recited in Table II, infra, other catalysts may be prepared. Table III lists the yields and catalyst compositions.

using an isobutylene feed gives 47.2% conversion with 80.8% selectivity to methacrolein.

TEST PROCEDURE

An 8.0 g sample of catalyst is packed in the bottom portion of a ⅜" O.D. 304SS "U" tube. The remainder of the tube is filled with Norton Denstone. The tube is installed in the reactor and the air feed is started to pressurize the system before isobutylene, tert-butanol, tert-butyl acetate or tert-butyl methyl ether feed is started. The reactor is run one hour to achieve steady state reactor operation. Sampling is then started and continued until the reactor product distribution achieves a steady state operation.

The composition of the feed stream is normally 4.9% of isobutylene or compound convertible to isobutylene, 60.0% air and 35.1% water. Total flow is about 1480

TABLE II

| Compounds | Ex.21 | Ex.22 | Ex.23 | Ex.24 | Ex.25 | Ex.26 | Ex.27 | Ex.28 | Ex.29 | Ex.30 |
|---|---|---|---|---|---|---|---|---|---|---|
| Ammonium Heptamolybdate | 42.8 | 42.8 | 42.8 | 42.8 | 42.8 | 42.8 | 42.8 | 42.8 | 42.8 | 42.8 |
| Nitric Acid (71%) | 20ml | 20ml | 20ml | 20ml | 20ml | 20ml | 20ml | 20ml | 20ml | 20ml |
| Bismuth Nitrate in Nitric Acid (71%) | 9.7 8ml | 9.7 8ml | 9.7 8ml | 9.7 8ml | 9.7 8ml | 9.7 8ml | 9.7 8ml | 9.7 8ml | 9.7 8ml | 9.7 8ml |
| Cesium Nitrate | 2.0 | 2.0 | 2.0 | 2.0 | 2.0 | 2.0 | 2.0 | 2.0 | 2.0 | 2.0 |
| Ferric Nitrate | 24.2 | 56.4 | — | 24.2 | 24.2 | 40.3 | 24.2 | 56.4 | 24.2 | 24.2 |
| Cobalt Nitrate | 23.4 | 29.2 | 23.4 | 23.4 | 23.4 | 17.5 | 29.2 | 29.2 | 17.5 | 17.5 |
| Nickel Nitrate | 29.2 | 5.8 | 35.0 | 29.2 | 29.2 | 17.5 | 17.5 | 5.8 | 5.8 | 5.8 |
| Copper Nitrate | — | 4.8 | 4.8 | 4.8 | 4.8 | 4.8 | 4.8 | 4.8 | 4.8 | 4.8 |
| Colloidal Silica | 40.0 | 40.0 | 40.0 | 40.0 | 40.0 | 40.0 | 40.0 | 40.0 | 20.0 | 40.0 |
| Zirconium Nitrate | — | 6.8 | 6.8 | 6.8 | 6.8 | 6.8 | 6.8 | 6.8 | 6.8 | 6.8 |
| Tellurium Dioxide | 2.2 | 2.2 | 2.2 | 2.2 | 4.4 | 2.2 | 2.2 | 2.2 | 2.2 | 2.2 |
| Antimony Pentoxide | 3.25 | 3.25 | 3.25 | 3.25 | 3.25 | 3.25 | 3.25 | — | 3.25 | 3.25 |
| Phosphoric Acid (85%) | 4.6 | 4.6 | 4.6 | 4.6 | 4.6 | 4.6 | 4.6 | 4.6 | 4.6 | 4.6 |
| Ammonium Hydroxide | 156.5 | 156.5 | 156.5 | 156.5 | 156.5 | 156.5 | 156.5 | 156.5 | 156.5 | 156.5 |
| Boric Anhydride | 0.5005 | — | — | — | — | — | — | — | — | — |
| Yttrium Nitrate | — | — | — | — | — | — | — | — | 0.2 | — |
| Lanthanum Nitrate | — | — | — | — | — | — | — | — | 0.25 | — |
| Praseodymium Nitrate | — | — | — | — | — | — | — | — | 0.85 | — |
| Ammonium meta Tungstate | — | — | — | — | — | — | — | — | — | 8.5 |
| Ammonium meta Vanadate | — | — | — | — | — | — | — | — | — | 2.3 |

TABLE III

| Ex. No. | Composition | Yield (grams) | Screened Material on 18 mesh (grams) | Weight (grams) After Calcining 8 hrs. at 500° C. |
|---|---|---|---|---|
| 21 | $Mo_{12}P_2Fe_3Co_4Ni_5BiSbCs_{.5}Te_{.7}B_{.7}O_x$ | 164.9 | 96.6 | 47.5 |
| 22 | $Mo_{12}P_2Fe_7Co_5NiBiSbZrCs_{.5}Te_{.7}CuO_x$ | 166.5 | 91.2 | 43.8 |
| 23 | $Mo_{12}P_2Co_4Ni_6BiSbZrCs_{.5}Te_{.7}CuO_x$ | 150.4 | 96.8 | 42.3 |
| 24 | $Mo_{12}P_2Fe_3Co_4Ni_5BiSbZrCs_{.5}Te_{.7}CuO_x$ | 178.9 | 107.3 | 51.3 |
| 25 | $Mo_{12}P_2Fe_3Co_4Ni_5BiSbZrCs_{.5}Te_{1.4}CuO_x$ | 185.2 | 112.7 | 52.9 |
| 26 | $Mo_{12}P_2Fe_5Co_3Ni_3BiSbZrCs_{.5}Te_{.7}CuO_x$ | 181.1 | 110.4 | 50.4 |
| 27 | $Mo_{12}P_2Fe_3Co_5Ni_3BiSbZrCs_{.5}Te_{.7}CuO_x$ | 176.6 | 115.5 | 54.3 |
| 28 | $Mo_{12}P_2Fe_7Co_5NiBiZrCs_{.5}Te_{.7}CuO_x$ | 184.5 | 118.2 | 58.8 |
| 29 | $Mo_{12}P_2Fe_3Co_3NiBiSbZrCs_{.5}Te_{.7}CuY_{.03}Pr_{.03}La_{.1}O_x$ | 177.9 | 118.0 | 42.2 |
| 30 | $Mo_{12}P_2Fe_3Co_3NiBiSbZrCs_{.5}Te_{.7}CuVW_{1.5}O_x$ | 165.7 | 110.8 | 57.7 |

EXAMPLE 31

Catalytic Oxidation of tert-Butanol

Passing tert-butanol in air over denstone at 370° C. in the reactor generates isobutylene and water quantitatively. When tert-butanol is used in place of isobutylene under the same reaction conditions over a catalyst of composition—$Mo_{12}P_2Fe_3Co_3Ni_5Sb_1Bi_1Zr_1Cu_1Te_{0.7}Cs_{0.5}O_x$ there is obtained a 37.5% conversion of the cracked tert-butanol to oxidized products with an 80.2% selectivity to methacrolein. The same catalyst mmoles/hour. Space time is calculated from catalyst volume and flow rate by the equation:

$$\frac{\text{Volume of catalyst (ml)}}{\text{flow rate (mmole/hr.)}} \times \frac{3600 \text{ sec./hr.}}{22.4 \text{ ml/mmole}}$$

Space times are usually in the range of from 1 to 3 seconds. Inlet pressure is normally 20 psig. Salt bath temperature is generally in the range of from 300° C. to 410° C. but normally is around 370° C.

The following Table IV illustrates the catalytic activity of some of the catalysts of this application. However all catalysts embraced by the generic formula will behave in a similar manner.

TABLE IV

| Ex. No. | | Conversion (%) | Selectivity (%) | Yield Methacrolein (%) |
|---|---|---|---|---|
| 1 | | 94.5 | 81.8 | 76.8 |
| 2 | | 88.0 | 82.2 | 63.1 |
| 3 | | 77.3 | 81.6 | 63.1 |
| 4 | | 94 | 74.1 | 70 |
| 5 | | 49.4 | 76.0 | 37.5 |
| 6 | | 68.8 | 81.6 | 56.1 |
| 7 | | 98.1 | 71.1 | 69.7 |
| 8 | | 83.1 | 81.8 | 67.9 |
| 9 | | 93.6 | 76.4 | 71.5 |
| 10 | | 93.7 | 80.4 | 75.3 |
| 11 | | 95.0 | 78.3 | 74.4 |
| 12 | | 95.4 | 75.8 | 72.3 |
| 13 | | 85.7 | 84.2 | 72.2 |
| 14 | (a) | 94.1 | 76.6 | 72.1 (calcining temp. 500°) |
| 14 | (b) | 75.6 | 77.3 | 58.4 (calcining temp. 575°) |
| 15 | | 93.6 | 76.4 | 71.5 |
| 16 | | 86.5 | 82.3 | 71.2 |
| 17 | | 92.8 | 76.7 | 71.2 |
| 18 | (a) | 91.0 | 76.6 | 69.7 (calcining temp. 500°) |
| 18 | (b) | 82.9 | 78.1 | 64.7 (calcining temp. 575°) |
| 19 | | 88.4 | 76.2 | 67.4 |
| 20 | | 89.1 | 73.1 | 65.1 |
| 21 | | 100 | 69.1 | 69.1 |
| 22 | | 83.7 | 82.4 | 69.0 |
| 23 | | 93.8 | 73.3 | 68.8 |
| 24 | | 83.1 | 81.8 | 68.0 |
| 25 | | 79.6 | 84.6 | 67.3 |
| 26 | | 83.7 | 78.8 | 66.0 |
| 27 | | 79.2 | 82.2 | 65.1 |
| 28 | | 83.7 | 82.4 | 69.0 |
| 29 | | 78.4 | 70.0 | 54.9 |
| 30 | | 95.0 | 63.8 | 60.6 |

What is claimed is:

1. A catalyst having the formula $Mo_aP_bFe_c$—$Co_dNi_eBi_fTe_gSb_hCs_iZr_jX_kO_x$ wherein when a is 12; b is 2; c is 1–7; d is 3–7; e is 1–5; f is 1; g is 0.7–1.4; h is 0–1; i is 0.5; j is 0–1.75; k is 0–1; x is a value determined according to the state of oxidation, and X is one or more elements selected from Cu, B or Al.

2. The catalyst according to claim 1 having the formula $Mo_{12}P_2Fe_{5-7}Co_{5-7}NiBiSbZr_{1-1.75}Cs_{0.5}Te_{0.7}O_x$ where x is a value determined according to the state of oxidation.

3. The catalyst of claim 2 having the molecular formula $Mo_{12}P_2Fe_5Co_5NiBiSbZrCs_{0.5}Te_{0.7}O_x$.

4. The catalyst of claim 2 having the formula $Mo_{12}P_2Fe_7Co_7NiBiSbZr_{1.25}Cs_{0.5}Te_{0.7}O_x$.

5. The catalyst of claim 2 having the molecular formula $Mo_{12}P_2Fe_7Co_7NiBiSbZr_{1.5}Cs_{0.5}Te_{0.7}O_x$.

6. The catalyst of claim 2 having the formula $Mo_{12}P_2Fe_5Co_5NiBiSbZr_{1.75}Cs_{0.5}Te_{0.7}O_x$.

7. The catalyst of claim 2 having the formula $Mo_{12}P_2Fe_5Co_5NiBiSbZr_{1.25}Cs_{0.5}Te_{0.7}O_x$.

8. The catalyst of claim 1 having the formula $Mo_{12}P_2Fe_7Co_7NiBiSbCs_{0.5}Te_{0.7}CuO_x$.

9. The catalyst of claim 1 having the formula $Mo_{12}P_2FeCo_5Ni_5BiSbZrCs_{0.5}Te_{0.7}CuO_x$.